United States Patent [19]

Duffett

[11] Plant 5,108

[45] Sep. 20, 1983

[54] CHRYSANTHEMUM PLANT

[75] Inventor: William E. Duffett, Salinas, Calif.

[73] Assignee: Yoder Brothers, Inc., Barberton, Ohio

[21] Appl. No.: 340,107

[22] Filed: Jan. 18, 1982

[51] Int. Cl.[3] ..... A01H 5/00

[52] U.S. Cl. ..... Plt./79

[58] Field of Search ..... Plt./79

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant known by the cultivar name Win and particularly characterized as to uniqueness by the combined characteristics of flat capitulum form, decorative capitulum type; orange-bronze ray floret color; diameter across face of capitulum ranging from 80 to 100 mm. at maturity; uniform ten week photoperiodic flowering response to short days; tall plant height when grown single stem; 17 to 24 cm. peduncles on open, normally terminal sprays, and 13° C. minimum temperature tolerance for initiation and development of flowering buds.

3 Drawing Figures

The present invention comprises a new and distinct cultivar of *Chrysanthemum morifolium,* Ramat., hereinafter referred to by the cultivar name Win.

Win is a product of a planned breeding program which had the objective of creating new chrysanthemum cultivars with low temperature tolerance in cut spray mum programs, decorative capitulum type, orange-bronze ray floret color, ten week flowering response, and having the ability to produce commercially acceptable quality in year round programs. Such traits in combination were not present in previously available commercial cultivars.

Win was originated from a cross made in a controlled breeding program in Salinas, Calif. in 1978. The female parent was a cultivar identified as #77212002 (unnamed seedling), originated from a hybridization of Solorama (U.S. Plant Pat. No. 3,673) and an unnamed seedling. The male parent of Win was a cultivar identified as #76188001 (unpatented), originated from a cross between two unnamed seedlings.

Win was discovered and selected as one flowering plant within the progeny of the stated cross by William E. Duffett on Feb. 25, 1979 in a controlled environment in Salinas, Calif.

The first act of asexual reproduction of Win was accomplished when vegetative cuttings were taken from the initial selection in May, 1979 in a controlled environment in Salinas, Calif. by a technician working under formulations established and supervised by William E. Duffett.

Horticultural examination of selected units initiated Dec. 3, 1979 has demonstrated that the combination of characteristics as herein disclosed for Win are firmly fixed and are retained through successive generations of asexual reproduction.

Win has not been observed under all possible environmental conditions. The phenotype may vary significantly with variations in environment such as temperature, light intensity and day length. The observations, measurements and comparisons describe plants grown in Salinas, Calif. under greenhouse conditions which approximate those generally used in commercial practice.

The following traits have been repeatedly observed and are determined to be basic characteristics of Win which in combination distinguish this chrysanthemum as a new and distinct cultivar:

(1) flat capitulum form;

(2) decorative capitulum type;

(3) orange-bronze ray floret color;

(4) diameter across face of capitulum ranging from 80 to 100 mm. at maturity;

(5) uniform ten week photoperiodic flowering response to short days;

(6) tall plant height (75 to 100 cm.) when grown from a rooted cutting with no long days and 14 hour dark periods for March through November flowerings, and (7) tolerance of 13° C. minimum temperature for initiation and development of flowering buds.

The accompanying photographic drawings depict typical foliage and inflorescence characteristics of Win. Sheet 1 is a color photograph of a plant of Win grown as a cut spray, with colors being as accurate as possible with renditions of this type. Sheet 2 is a black and white photograph of three views of theinflorescence of Win. Sheet 3 shows the foliage of Win in three stages of growth.

Of the many commercial cutlivars known to the present inventors, the most similar in comparison to Win is Flame Belair (U.S. Plant Pat. No. 3,353). Reference is made to attached Chart A which compares certain characteristics of Win to those same characteristics of Flame Belair.

In comparison to Flame Belair, Win has a more terminal, upright spray formation, less open and seldom compound; diameter across face of capitulum is larger by 10 to 20 mm.; plant height is taller by 5 to 20 cm.; and flowering response is slower by 1 week but more uniform and more tolerant of both high and low temperatures. The capitulum form, capitulum type and ray floret color of Win are similar to those same characteristics of Flame Belair.

In the following description, color references are made to The Royal Horticultural Society Colour Chart. The color values were determined between 4:00 and 4:30 P.M. on Oct. 21, 1981 under 150 foot-candle light intensity of Salinas, Calif.

Classification:

*Botanical.*—*Chrysanthemum morifolium,* Ramat., cv Win.

*Commercial.*—Cut spray.

INFLORESCENCE

A. Capitulum:

*Form.*—Flat.

*Type.*—Decorative.

*Diameter across face.*—80 to 100 mm.

B. Corolla of ray florets:

*General tonality from a distance of three meters*—Orange-bronze; 24-A.

*Color (abaxial).*—25-A and B (immature) to 23-A and B (mature).

*Color (adaxial).*—14-C (immature) to 17-D (mature).

C. Reproductive organs:

*Androecium.*—Present disc florets only; scant pollen.

*Gynoecium.*—Present both ray and disc florets.

PLANT

A. General appearance:

*Height.*—Very tall (75 to 100 cm.) as a flowering plant from a rooted cutting, with no long days for March through November flowerings and maintaining a minimum nightly 14 hour continuous dark period.

B. Foliage:

*Color (abaxial).*—147-A.

*Color (adaxial).*—191-A.

*Shape.*—Deeply lobed and deeply serrated.

CHART A

COMPARISON OF WIN AND FLAME BELAIR

| CULTIVAR | RAY FLORET COLOR | CAPITULUM FORM AND TYPE | SPRAY FORMATION |
|---|---|---|---|
| WIN | Orange-Bronze | Flat Decorative | Terminal Upright |
| FLAME BELAIR | Bronze | Flat Decorative | Terminal open, sometimes compound |

| CULTIVAR | DIAMETER ACROSS FACE OF CAPITULUM | PLANT HEIGHT | FLOWERING RESPONSE PERIOD |
|---|---|---|---|
| WIN | 80 to 100 mm. | Very Tall 75 to 100 cm. | 10 Week |
| FLAME BELAIR | 70 to 80 mm. | Tall 70 to 80 cm. | 9 Week |

COMPARISONS MADE OF PLANTS GROWN AS SINGLE STEM CUT SPRAYS IN SALINAS, CALIFORNIA

I claim:

1. A new and distinct plant of *Chrysanthemum morifolium,* Ramat., known by the cultivar name of Win, as described and illustrated, and particularly characterized as to uniqueness by the combined characteristics of flat capitulum form; decorative capitulum type; orange-bronze ray floret color; diameter across face of capitulum ranging from 80 to 100 mm. at maturity; uniform ten week flowering response; tall plant height when grown single stem; 17 to 24 cm. peduncles on open, normally terminal sprays, and 13° C. minimum temperature tolerance for initiation and development of flowering buds.

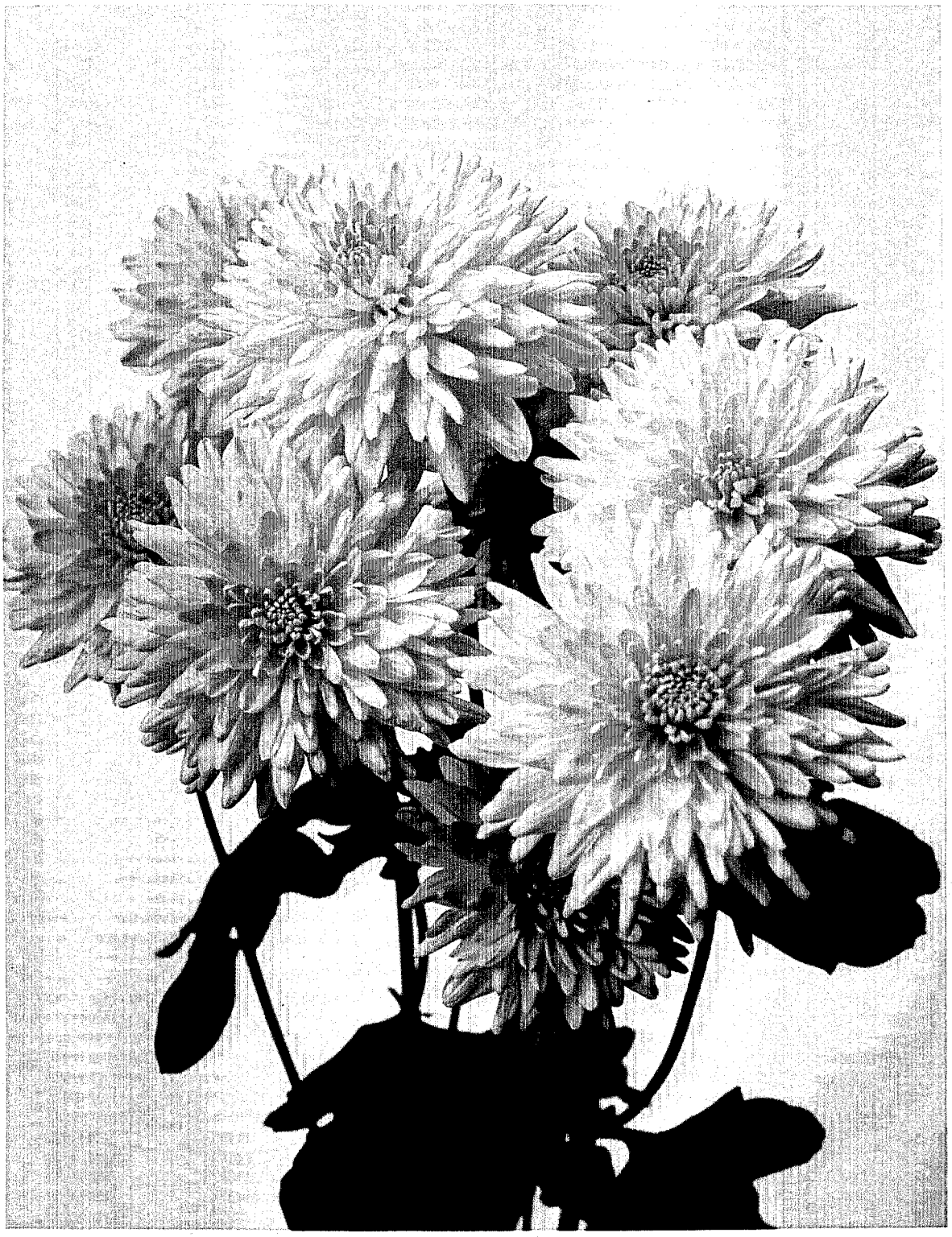

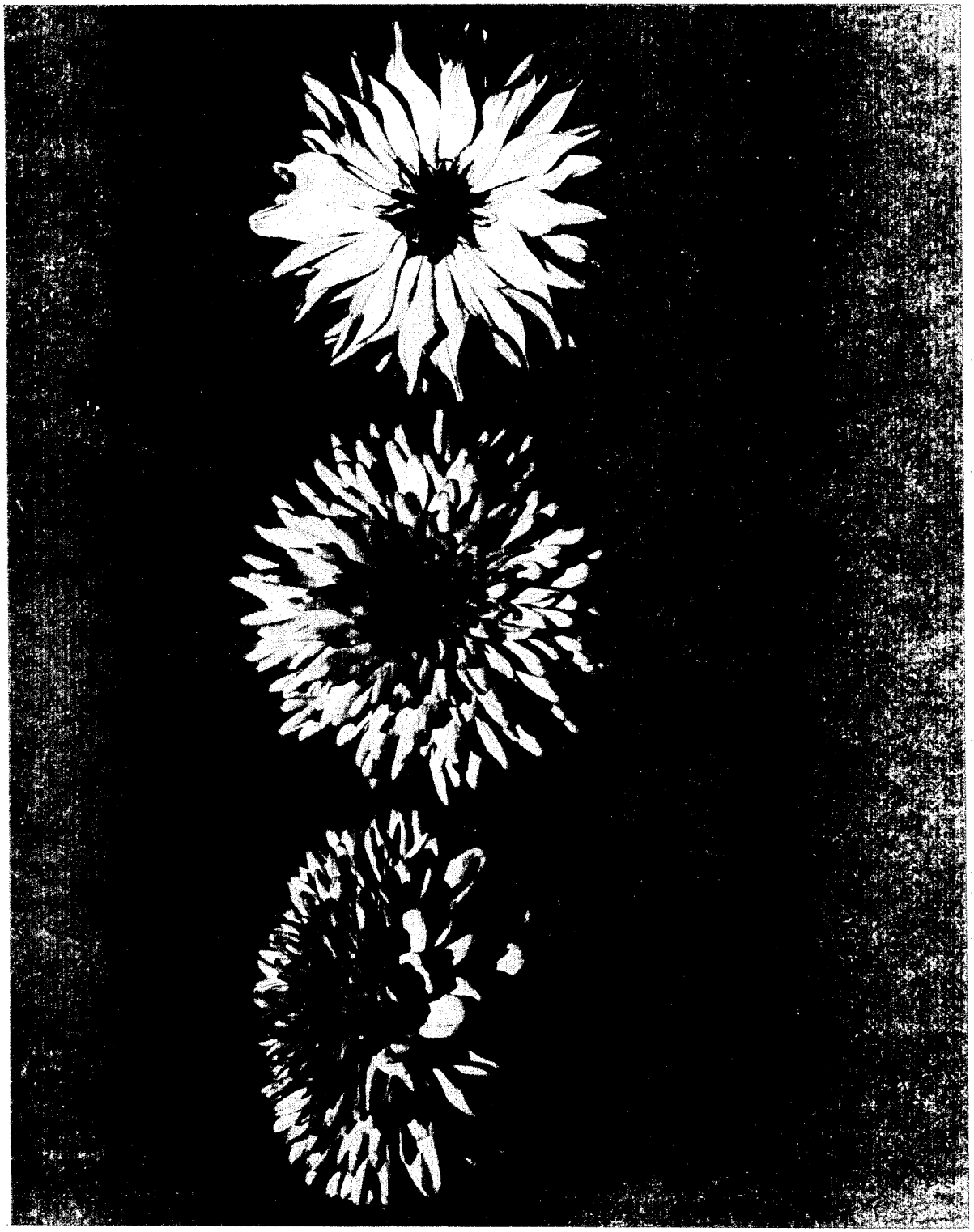

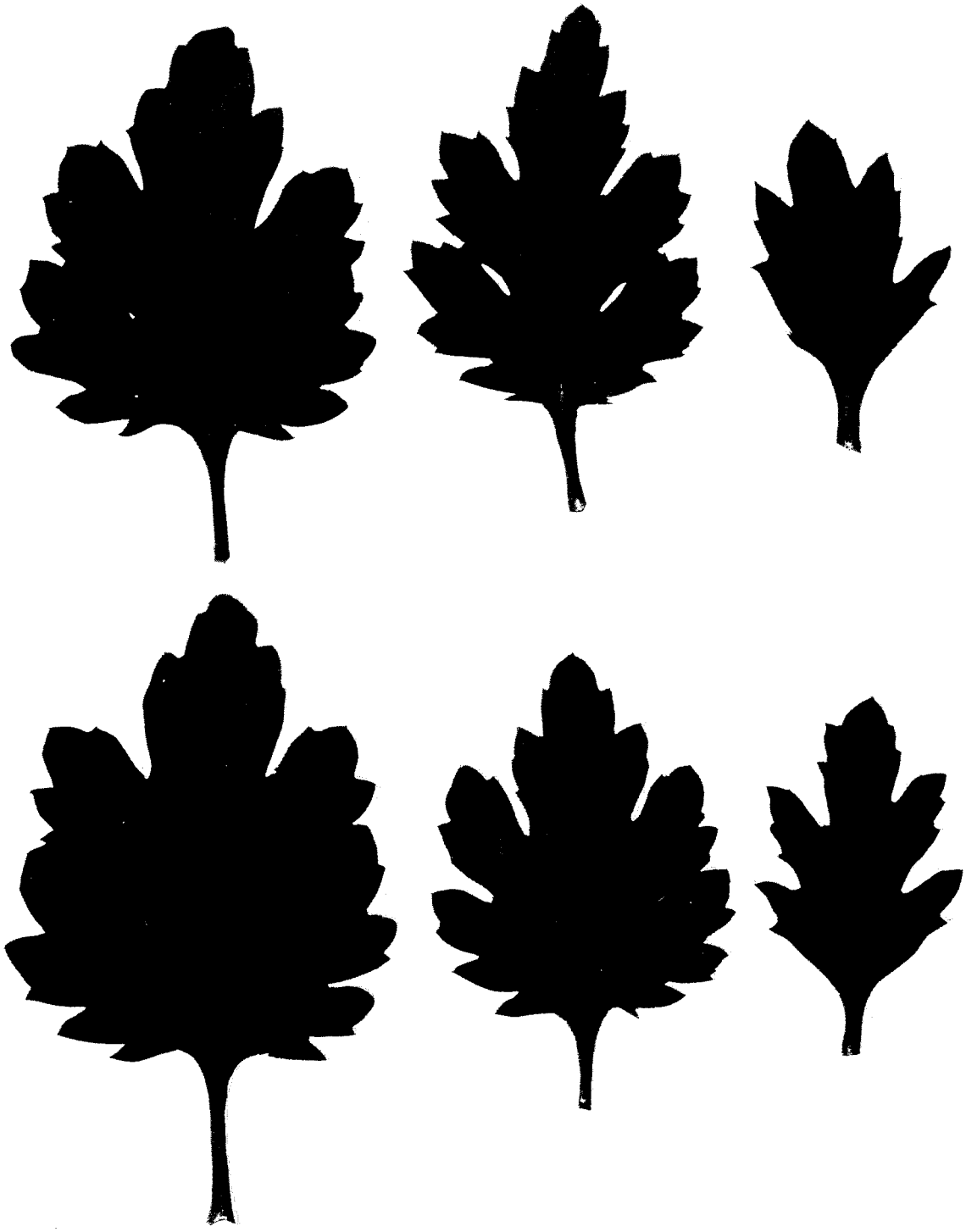

* * * * *